United States Patent [19]

Arita et al.

[11] Patent Number: 4,571,999

[45] Date of Patent: Feb. 25, 1986

[54] ULTRASONIC INSPECTING APPARATUS

[75] Inventors: Kishio Arita, Tokyo; Susumu Mitani, Saitama; Hideo Sakai, Saitama; Yoshikazu Sudo, Saitama; Yoshitaka Koide, Tokyo; Haruzi Sato, Kanagawa; Yoshio Habuka, Kanagawa; Takashi Kozakai, Kanagawa; Hiroji Tanaka, Kanagawa, all of Japan

[73] Assignees: Nippon Telegraph and Telephone Public Corporation; Mitsubishi Denki Kabushiki Kaisha, both of Tokyo, Japan

[21] Appl. No.: 602,371

[22] Filed: Apr. 20, 1984

[30] Foreign Application Priority Data

Apr. 23, 1983 [JP] Japan ................... 58-71995

[51] Int. Cl.$^4$ ............................. G01N 29/04
[52] U.S. Cl. ........................... 73/598; 73/602
[58] Field of Search ............... 73/598, 602, 622, 638

[56] References Cited

U.S. PATENT DOCUMENTS 3,521,483 7/1970 Miller et al. ..................... 73/598
3,600,937 8/1971 Nilberg ........................... 73/598
3,664,180 5/1972 McDonald et al. ............... 73/598

FOREIGN PATENT DOCUMENTS 219853 2/1968 U.S.S.R. ........................... 73/598

OTHER PUBLICATIONS

Japanese Utility Model Laid-Open Nos. 72580/78, 79091/78, 69287/78.
Escape from Hospital, The Asahi (Evening Edition), Feb. 14, 1983.
Tsuken Monthly Report 36-4, (1983).

Primary Examiner—Anthony V. Ciarlante
Attorney, Agent, or Firm—Bernard, Rothwell & Brown

[57] ABSTRACT

In an ultrasonic inspecting apparatus, propagation time is measured between a transmitting point of an ultrasonic wave from outer circumference of a subject material and a receiving point of the ultrasonic wave at another point on the outer circumference spaced apart from the transmitting point by a predetermined angle, and a predetermined sequence of operations is performed with the measured propagation times and the known constants, thereby internal information concerning the material, including location and shape of a defect existing therein, is provided.

2 Claims, 8 Drawing Figures

ULTRASONIC INSPECTING APPARATUS

BACKGROUND OF THE INVENTION

1. Field of the Invention

This invention relates to apparatuses which provide internal information of a specimen by measurement of propagation time of ultrasonic wave traveling through the specimen, and more particularly to an apparatus for detecting a defect within a wooden pole and displaying information of the defect in graphical form.

2. Description of the Prior Art

In a wooden pole, an internal defect, such as rotten part which cannot be seen from outside may develop sometimes as years pass. In order to detect such a defect, various means have been developed, for example, means for boring a hole in a wooden pole by a drill as disclosed in Japanese utility model, publication No. 53-72580, and means for driving a probe into a wooden pole as disclosed in Japanese utility model, publication No. 53-79091. These techniques have disadvantages in that holes must be made in the wooden pole in order to perform the inspection. Also in order to detect existence of a defect by means of ultrasonic wave, there is another means for transmitting ultrasonic wave in closed contact state to a wooden pole as disclosed in Japanese utility model publication No. 53-69287. By using this means existence of the defect may be detected, but it cannot provide defect information in quantative form.

In Japanese newspaper "Asahi" dated Feb. 14, 1983, technique is reported where inside of a pole, even growth rings can be investigated by the computer tomography using X-ray owing to significant technical progress in recent years. Since such a technique uses X-ray the measuring apparatus becomes of considerable size which make it unpracticable for inspecting the pole. In Monthly Report of Electric Communication Research Institute (Japan) No. 36-4 (1983), it is set forth that ultrasonic propagation time is measured on diameter of a wooden pole and on a position perpendicular to the projecting direction of ultrasonic wave thereby existence of a defect in the wooden pole is detected and further location or depth of the defect is provided.

It is known well that, as the frequency of an ultrasonic wave increases, rectilinearity of propagation of the wave through a body is increased and therefore the resolving power required to investigate internal state of the body is improved, while the amount of attenuation is also increased. Consequently, an apparatus using an ultrasonic wave in high frequency region is required to generate high output power which makes it uneconomical.

An apparatus, such as a wood tester WTD-II of Eisho Denshi K.K. or a concrete testing machine of Cho-onpa Kogyo K.K., may be commercially available, in which an ultrasonic wave of relatively low frequency (50 kHz–100 kHz) is used and relation between the delay time and length of known defect within a subject is previously determined by means of experiment, and on the basis of this relation length of the defect is presumed from data of the delay time actually measured.

Any of above-mentioned means in the prior art, however, cannot provide information which locates the defect within a body. It is often required in maintenance concerning a pole that the information of the defect be obtained and adequate time for repair or exchange is provided.

SUMMARY OF THE INVENTION

An object of the invention is to provide an apparatus for diagnosing the internal state of a specimen by using an ultrasonic wave of relatively low frequency and output power.

Another object of the invention is to provide an apparatus for diagnosing the internal state of a specimen from propagation times of an ultrasonic wave transmitted from several points into the specimen.

Another object of the invention is to provide an ultrasonic inspecting apparatus for scanning a specimen from outer surface along a specific cross-section thereof by using an ultrasonic wave, and displaying information of state of the cross-section in graphical form.

Another object of the invention is to provide an apparatus for scanning a defect within a specimen by an ultrasonic wave, and displaying information to locate the defect in graphical form.

According to the invention, various points on outer circumference of a specimen are selected in sequence and propagation time of ultrasonic wave is measured between the transmitting point of the ultrasonic wave and the receiving point of the ultrasonic wave, which is located on the outer circumference at a point spaced apart by a predetermined angle with respect to said transmitting point, and predetermined operations are performed using known constants relating to the specimen, reference propagation time of the ultrasonic wave, which is measured at a sound portion of the specimen, thereby information is provided regarding the location and shape of the defect existing in a specified portion of the cross-section of the specimen.

Constants to be used in these operations may be set approximately in accordance with characteristic response derived from measurements of propagation time of ultrasonic wave traveling through a defect of known size and known position provided within a column having same or equivalent material to that of the specimen.

DETAILED DESCRIPTION OF THE INVENTION

An ultrasonic inspecting apparatus embodying the present invention will now be described in detail referring to the accompanying drawings.

Figure 1:
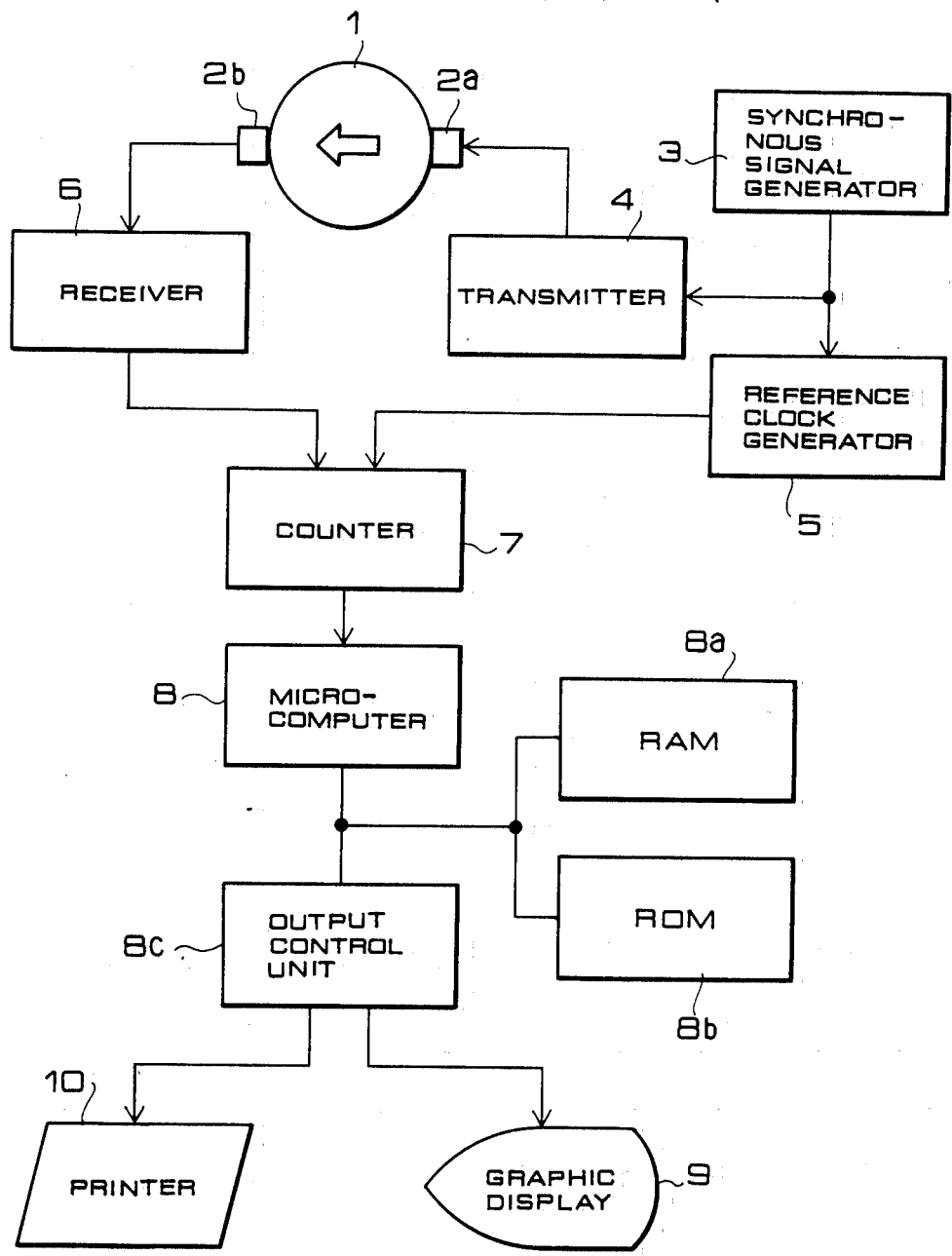
FIG. 1 is a block diagram of an ultrasonic inspecting apparatus embodying the present invention.

FIG. 1 is a block diagram illustrating the constitution of the invention, wherein numeral 1 designates a measuring cross-section of a specimen, such as a wooden pole. On the outer periphery of the cross-section are arranged an ultrasonic transmitting element 2a using a vibrator of Langevin type and a ultrasonic receiving element 2b. A synchronous signal generator 3 is provided for generating a synchronous signal to allow various parts of the apparatus to operate synchronously. A transmitter is provided for driving the transmitting element 2a. The generator 3 and the transmitter 4 are connected to a clock generator 5 which generates a reference clock signal for clocking them. The transmitting element 2a driven by the transmitter 4 generates ultrasonic wave which is directed to the center of the measuring cross-section 1 so as to pass through the center. The ultrasonic wave coming from the center direction is received for converting it into electric signal by the receiving element 2b and supplied to a receiver 6. Reference clock signal generated by the generator 5 is also provided to a counter 7 which starts counting when the transmitting element 2a becomes active to send the ultrasonic wave into the specimen, and stops counting when the receiver 6 receives it. Consequently, the counter 7 has the counting result representing the measured propagation time Ti (i=1, 2, ...) required for the ultrasonic wave to travel through the cross-section 1. This result is stored by a microcomputer 8 in a random access memory (RAM) 8a connected thereto. A read only memory (ROM) 8b in which programs to perform various operations relating to measurement are stored as hereinafter described is also connected to the microcomputer 8. Further, through an output control unit 8c, a graphic display 9 and/or a printer 10 for outputting the measuring result in graphical form are connected to the microcomputer 8.

Either display 9 or the printer 10 may be provided if only information of the location and shape of the defect determined by the microcomputer 8 in the measuring cross-section 1 is required to be output in a graphic form.

Figure 2:
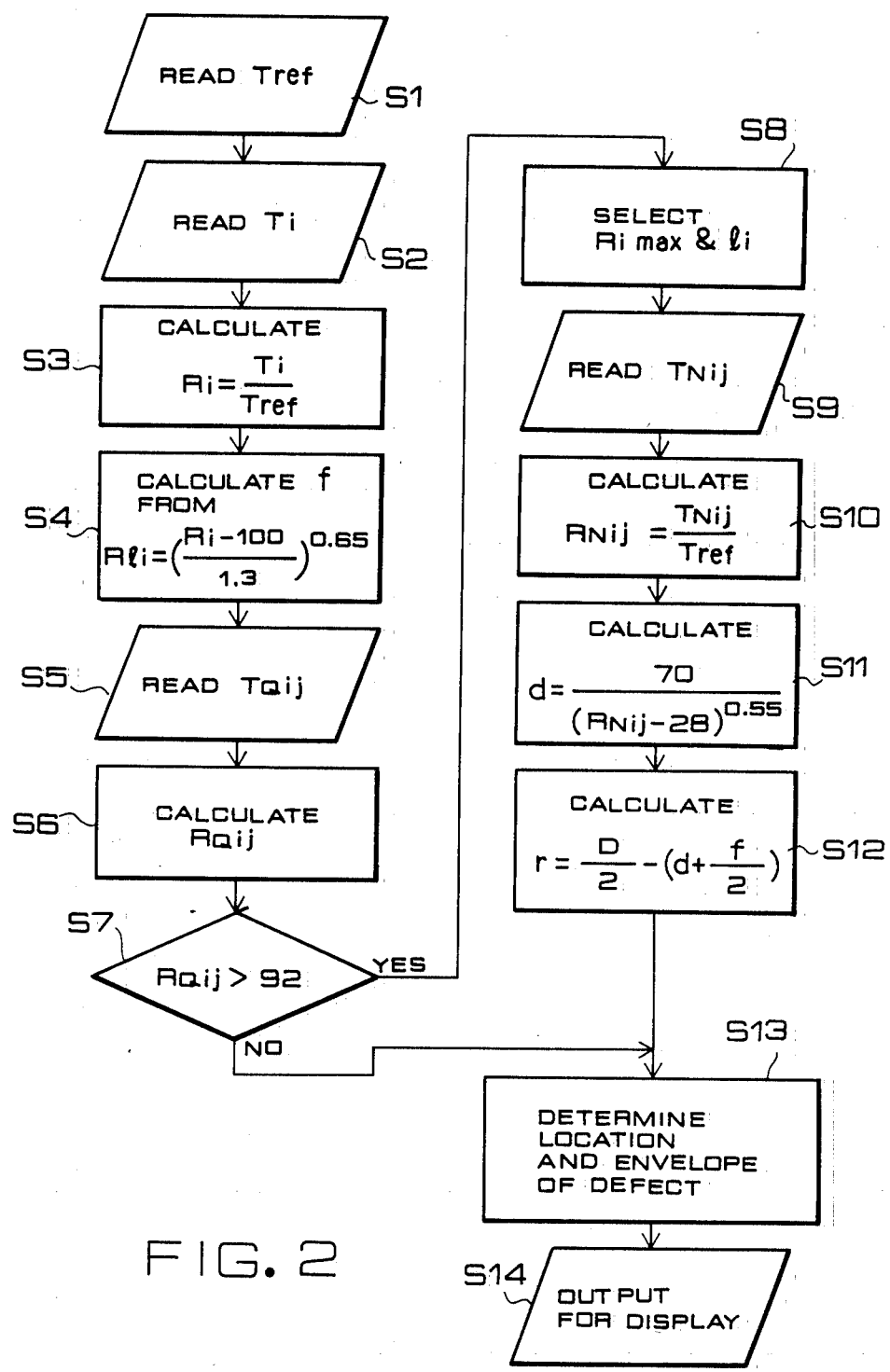
FIG. 2 is a flow chart illustrating operation of the apparatus shown in FIG. 1.

Operation of the embodiment will now be described referring to a general flow chart shown in FIG. 2.

In step 1, reference propagation time $T_{ref}$ is measured. The reference propagation time is defined as a time required for the ultrasonic wave to travel through distance of diameter D of a pole, which does not contain a defect which causes deterioration of the strength of the pole i.e. the pole is sound. The measurement of the reference propagation time $t_{ref}$ is preferably made with the transmitting element 2a contacted to outer circumferential surface of the upper part of the pole before the ultrasonic wave is transmitted through the diameter of the pole, and the ultrasonic wave is received by the receiving element 2b contacted at opposite side of the pole with respect to the pole center and the transmitting element 2a, and the propagation time $T_{ref}$ is thus measured between both elements and stored by the microcomputer 8 as data in the RAM 8a. The reason why the measurement is performed at the upper portion of the pole is that this portion usually contains no rotten part so that the time $T_{ref}$ is conveniently determined.

In step $S_2$, ultrasonic propagation time Ti is measured at respective positions including the center of the pole to be measured and being spaced apart 180° with each other.

Figure 3:
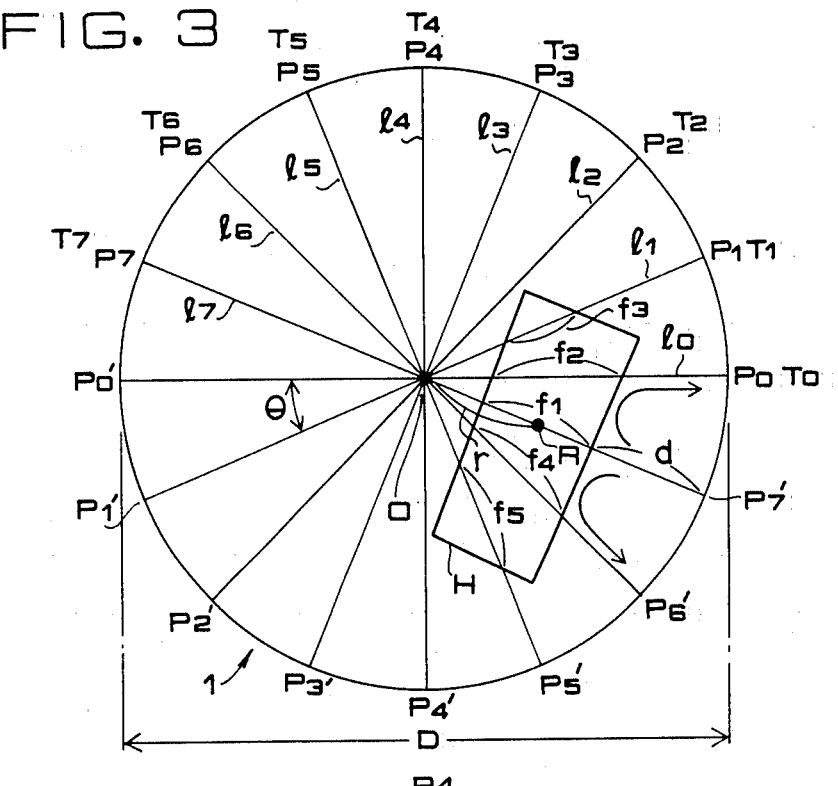
FIG. 3 is a diagram illustrating coordinate positions of transmitting an ultrasonic wave to a specimen and receiving an ultrasonic wave from a specimen.

FIG. 3 is a diagram showing an imaginary measuring cross-section 1 of the pole cut in the horizontal direction. Reference character H in the figure designates the defect. The defect in this case has a known position since it is artificially made for simplifying the description. Each of lines $1_0, 1_1, \ldots 1_7$ passes through the center 0 of the cross-section 1 and has known length, and adjacent lines are preferably spaced from each other by an angle of $\theta = 22.5°$.

The transmitting and the receiving element 2a and 2b are contacted with the outer circumference of the pole respectively at points $P_o$ and $P_o'$ as shown in FIG. 3, and the propagation time $T_o$ between points $P_o$-$P_o'$ is measured. Subsequently the propagation time $T_1$ between $P_1$-$P_1'$, time $T_2$ between $P_2$-$P_2'$ ... time $T_7$ between $P_7$-$P_7'$ are measured in sequence. Each of the propagation times $T_o$-$T_7$ is stored in the RAM 8a under the control of the microcomputer 8.

In step $S_3$, the microcomputer 8 estimates the ratio Ri (%) (i=0, ..., 7) of time $T_0$-$T_7$ with respect to the propagation time $T_{ref}$. In this case, the ratio Ri becomes 100% in lines $1_2$, $1_3$ and $1_4$ which do not pass through the defect H. On the contrary, the ratio Ri is beyond 100% in lines $1_0$ and $1_7$ with which pass through the defect H. Typically, the propagation time of the ultrasonic wave in the defect or hollow portion takes more time than the sound portion.

In step $S_4$, length f of the defect H having the propagation time ratio Ri exceeding 100% is estimated.

Figure 4:
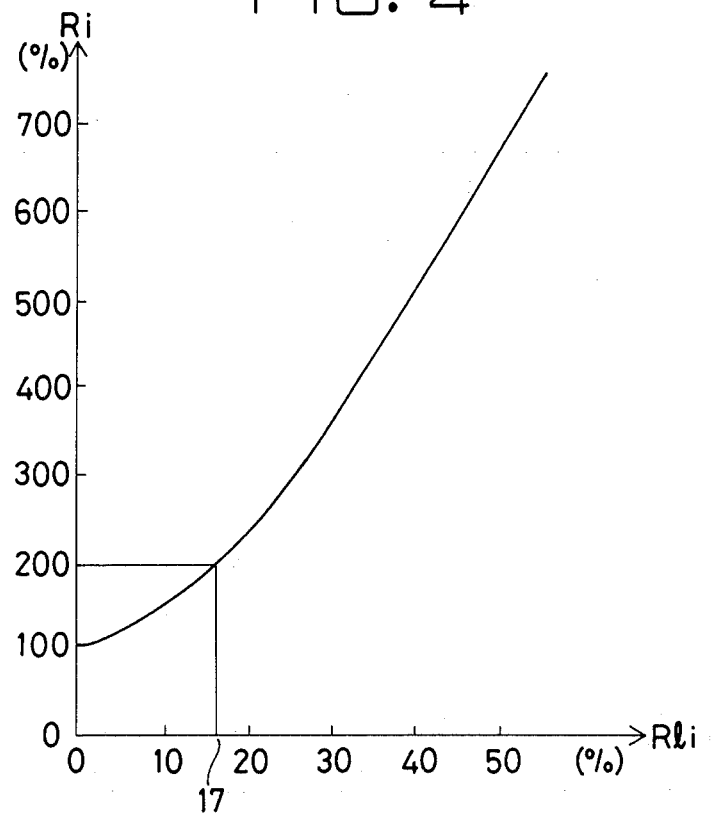
FIG. 4 is a characteristic diagram illustrating the relation between length ratio of a defect within the specimen and propagation time of ultrasonic wave.

In usual, ratio f/D between the length f and the diameter D of wood, i.e. the defect length ratio R1i is correlated to the ratio Ri as shown in FIG. 4, wherein ordinate represents the ratio Ri and abscissa the ratio R1i. The rot degree curve shown in the figure may be related by the following approximate formula.

$$R1i \approx [(Ri - 100)/1.3] 0.65 \quad (1)$$

If the ratio Ri is 200%, the ratio R1i is estimated 17% by equation (1). Consequently, the length f of the defect H is estimated by operation of diameter $D \times 0.17$ since f/D = R1i.

In step $S_5$, propagation time ratio at position of 90°, i.e. $R_Qij$ (i, j=0, 1, ..., and orthogonal with each other) is measured. In this step, decision is made regarding which of four quadrants contains the defect, the first quadrant defined by line $P_oO$ and line, the second quadrant defined by line $P_4O$ and line $P_o'O$, the third quadrant defined by line $P_o'O$ and line $P_4'O$ or the fourth quadrant defined by line $P_4'O$ and line $P_oO$. For example, when the transmitting element 2a is contacted to the point $P_o$ so that ultrasonic wave is directed to the center O and the receiving element 2b is contacted to the point $P_4$ on orthogonal line to the line $P_oO$, the ultrasonic propagation time $T_{Qo4}$ between points $P_o$-$P_4$ is measured and read into the microcomputer 8.

In step $S_6$, the measured time $T_Qij$ (i, j=0, 1 ...) is divided by the reference propagation time $T_{ref}$, that is, $T_Qij/T_{ref}$ which determines the propagation time ratio $R_Qij$. The measurement is performed for the paths via the center O between points $P_o$-$P_4$, $P_4$-$P_o'$, $P_o'$-$P_4'$ and $P_4'$-$P_o$. In this case, the ratio $R_Qij$ becomes 92% in the second and third quadrants since they do not contain the defect H, but it exceeds 92% in the first and fourth quadrants since they contain the defect H.

In step $S_7$, the microcomputer 8 decides whether or not the ratio $R_{Qij}$ exceeds 92%, which is selected from the experimental measurement as a criterion for representing the existence of the defect. If it does, then proceed to step $S_8$; if not, proceed to step $S_{13}$.

In step $S_8$, maximum value of the ratio Ri obtained by the measurement in step $S_3$, i.e. Ri max, is selected, and line corresponding to Ri max, for example, line $l_7$ is selected.

In step $S_9$, the transmitting element $2a$ is contacted to the point $P_7'$ at which the line $l_7$ intersects the outer circumferential line of the measuring cross-section 1 in the first and fourth quadrants which are decided to have a defect respectively by steps $S_7$. While the receiving element $2b$ is contacted to the point $P_o$ and/or the point $P_6'$ being adjacent to $P_7'$ by an angle of 22.5° and receives the ultrasonic wave, thereby the ultrasonic wave propagation times $T_N7'o$ and $T_N7'6'$ are measured for the paths via the center O between points $P_7'-P_0$ and $P_7'-P_6'$ and read into the microcomputer 8.

In the step $S_{10}$, the microcomputer 8 divides the measured time $T_Nij$ (i=0, 1 . . . ; j=0' . . . 7' and spaced to each other by angle 22.5°) by the reference propagation time $T_{ref}$ so as to determine the propagation time ratio $R_Nij$.

In step $S_{11}$, the microcomputer 8 estimates depth d from the ratio $R_Nij$ using operation formula as hereinafter described.

Figure 5:
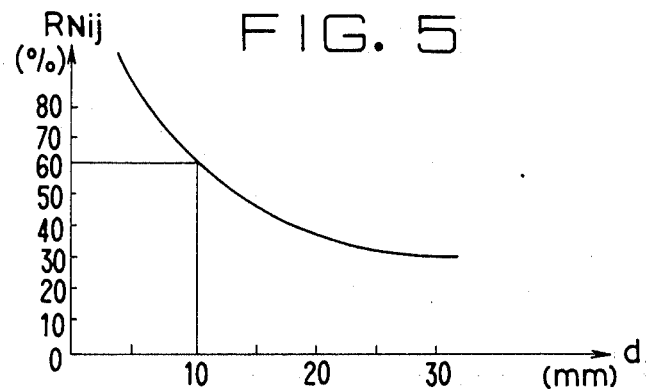
FIG. 5 is a characteristic diagram illustrating the relation between the distance of the defect from the specimen surface and the propagation time ratio.

Generally, from experimental measurements of various rotten portions, relation between depth d of the defect portion from the outer circumferential surface and the propagation time ratio $R_Nij$ in adjacent positions spaced apart by an angle of 22.5° may be expressed by a graph shown in FIG. 5, wherein ordinate represents the propagation time ratio $R_Nij$ and abscissa the depth d from the outer circumferential surface.

The characteristic curve shown may be related by the following approximate formula;

$$d \approx 70/(R_Nij-28)^{0.55} \qquad (2)$$

For example, if the ratio $R_Nij$ is 60%, it gives the depth d of 10 mm by the calculation using equation (2). If the wood pole is sound, it provides approximately 30% of the propagation time ratio $R_Nij$ for the path between points spaced apart from each other by 22.5°.

In step $S_{12}$, the location and shape of the defect are determined. Using the line segments $f_1-f_5$ and the depth d which have been already calculated, the microcomputer 8 calculates length r extending from the center O to the middle point of line segment $f_r$.

In step $S_{13}$, a circle having radius r and the center O is drawn. Assuming that each of middle points of line segments $f_1-f_5$ exists on the circumference, locations of the line segments $f_1-f_5$ are determined on the lines $l_7$, $l_o$, $l_1$, $l_6$ and $l_5$, respectively. The shape of the defect is generated from envelopes at both ends of each segment.

Figure 6:
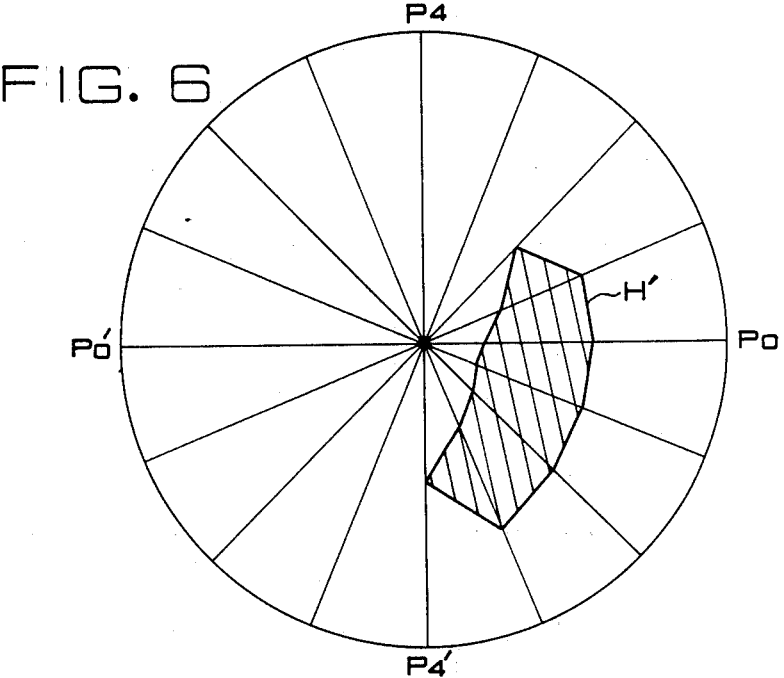
FIG. 6 is a diagram illustrating the location and shape of the defect determined from the measured ultrasonic propagation time in the specimen by the present invention.

In step $S_{14}$ the microcomputer 8 provides the resulting data of the envelopes to the graphic display 9 and/or the printer 10, which display them as shown in FIG. 6.

FIG. 6 shows a defect H' which is determined by above-mentioned sequence of operations and displayed on the display. As clearly seen from the figure, the appearance of the defect H' may be well approximated to the defect H shown in FIG. 3.

Figure 7:
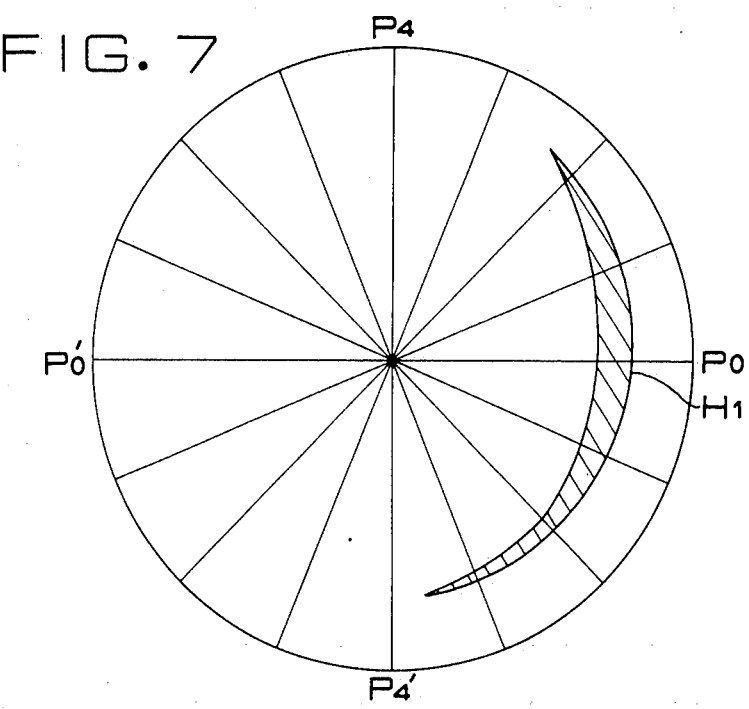
FIG. 7 is a diagram illustrating the location and shape of a defect in another specimen.
Figure 8:
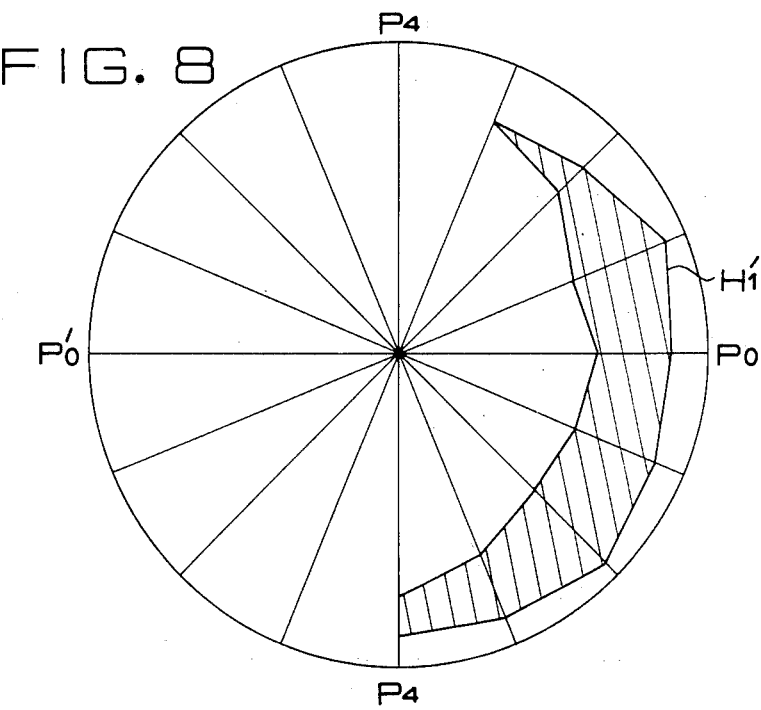
FIG. 8 is a diagram illustrating the location and shape of the defect in the specimen of FIG. 7 determined by the present invention.

FIG. 7 shows a sectional view of another wooden pole in which a defect $H_1$ is actually provided, and FIG. 8 is a view of a defect $H_1'$ obtained by the measurements of the defect $H_1$ shown in FIG. 7 and displayed in graphic form by the above mentioned apparatus of the invention. It is clearly seen also that the defect $H_1'$ has good coincidence in shape with the defect $H_1$.

A specific embodiment of the invention has been hereinbefore described. However, it is clear that various modifications may be made without departing from the spirit and the scope of the invention, and any of the modifications shall be included in the invention.

What is claimed is:

1. An ultrasonic inspecting apparatus comprising:
   means for measuring propagation time between one point sequentially selected on the outer circumference of a specimen for transmitting an ultrasonic wave directed to the center of the specimen and another point on the outer circumference spaced apart from said selected point by a predetermined angle for receiving the ultrasonic wave;
   data processing means for sequentially reading data of the propagation time measured by said measuring means and performing predetermined operations with reference propagation time of the ultrasonic wave measured at a sound portion of the specimen to provide data representing the state of cross-section at a predetermined portion of the specimen; and
   means for displaying said data provided from the data processing means in graphical form;
   said data processing means including:
   (1) means for selecting propagation time of the ultrasonic wave traveling through the diameter of a sound portion of the specimen as a reference propagation time;
   (2) means for determining a first ratio between propagation time of an ultrasonic wave traveling through the diameter of the measuring cross-section of the specimen and the reference propagation time at plural points on the circumference of the specimen;
   (3) means for substituting the first ratio in a predetermined first calculation formula $$f = (Ri - 100/1.3)\, 0.65_D$$

where f=length of the defect, Ri=first ratio, D=diameter of specimen, for determining the length of the defect;
   (4) means for determining a second ratio which is derived from the ultrasonic propagation time between the transmitting point of the ultrasonic wave and the receiving point on the outer circumference of the specimen spaced apart from the transmitting point by 90°, and the reference propagation time at plural points on the outer circumference;
   (5) means for determining that the portion having the second ratio which is greater than a predetermined reference value has a defect;
   (6) means for determining a third ratio which is derived from ultrasonic propagation time between the transmitting point of an ultrasonic wave and the receiving point on the outer circumference of the specimen spaced apart from the transmitting point by a predetermined angle less than 90° and the reference propagation time at plural points on the outer circumference;
   (7) means for substituting the third ratio in a predetermined second calculation formula $$d = 70/(R_{Mij} - 28)^{0.55}$$

where d=depth from the outer circumferential surface of the specimen to the defect, $R_{Mij}$=third ratio, for determining the depth from the outer circumferential surface to the defect;

(8) means for substituting length and depth of the defect in a predetermined third calculation formula $$r = D/2 - (d + f/2)$$

where r=center radius of the defect, for determining the center radius of the defect; and (9) means for displaying the state of the cross-section including the defect in graphical form on the basis of the center position and the length of the defect.

2. An inspecting apparatus as set forth claim 1 wherein the defect existing within the specimen has ultrasonic propagation time longer than that of the sound portion of the specimen.

* * * * *